(12) United States Patent
Webler, Jr.

(10) Patent No.: US 8,490,626 B2
(45) Date of Patent: Jul. 23, 2013

(54) ELECTRODE DATA ANALYSIS TO INDICATE CATHETER STABILITY AND/OR NEEDLE PENETRATION SUCCESS

(75) Inventor: William E. Webler, Jr., San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1214 days.

(21) Appl. No.: 12/342,018

(22) Filed: Dec. 22, 2008

(65) Prior Publication Data

US 2010/0160769 A1 Jun. 24, 2010

(51) Int. Cl.
*A61B 19/00* (2006.01)

(52) U.S. Cl.
USPC .......................................................... 128/897

(58) Field of Classification Search
USPC .................................................. 128/897–898
See application file for complete search history.

*Primary Examiner* — John Lacyk
(74) *Attorney, Agent, or Firm* — Blakely, Sokoloff, Taylor & Zafman LLP

(57) ABSTRACT

Determining stability of a catheter is described. A first signal originating from a first region of a patient is monitored and a second signal originating from a second region of the patient is monitored. First components from a recurring interval of the second signal are extracted, where the recurring interval is defined by the first signal. The first components are compared to determine a first similarity value of the first components over time. The first similarity value is compared to a threshold value to determine a stability evaluation for a source of the second signal.

20 Claims, 21 Drawing Sheets

ELECTRODE DATA ANALYSIS TO INDICATE CATHETER STABILITY AND/OR NEEDLE PENETRATION SUCCESS

FIELD

This invention relates generally to catheter-based medical treatment, and more specifically to measuring the stability of a catheter or a device coupled to the catheter at a treatment region.

BACKGROUND

Congestive heart failure is a major disease with a high mortality rate. The disease progresses continuously, the causes being compensation of the heart muscle to make up for the loss of function due to ischemic (i.e., restriction in blood supply) and infarcted (i.e., necrotic tissue resulting from restriction in blood supply) myocardium, mechanical deformation of weakened wall structures, valve regurgitation and other disease states. As the heart compensates, over-working the still functioning regions of the myocardium, more tissue becomes ischemic and infarcted, and the heart chamber expands in size due to weakened infarcted regions until the anatomical valve structures can no longer operate properly.

In other cases, the wall of the heart thickens to the point that the ventricle(s) are no longer able to effectively dilate to fill properly and/or to contract properly. The resulting complications due to low cardiac output and pulmonary hypertension become progressively more debilitating, leading to death. Existing methods for treating congestive heart failure include drugs to control heart rate, blood volume, myocardial contractility and/or blood pressure, the removal of infarcted or hypertrophied tissue/ventricular re-sectioning, valve repair and/or valve annular re-shaping and the mechanical constraint of the heart chamber.

Another approach for treating ischemic or infarcted myocardial tissue is the implantation of cells, such as mesenchymal stem cells, skeletal myoblasts, bone marrow mononuclear cells, etc., which will facilitate the revitalization of ischemic and/or infarcted heart tissue. Other approaches include the injection of a gene or a gene(s) in vectors/delivery micelles to cause local cells to produce substances to control the growth of desired tissues such as myocardium and/or blood vessels. Other approaches also include the injection of a stabilizing, reinforcing or bulking material(s) into infarcted and/or thinned tissue to mechanically reinforce it, such that its expansion/thinning, and the resulting expansion of the ventricular volume, may be slowed or halted. Two or more of these approaches may be combined. Hereafter, these types of materials, as well as solutions containing them, will be referred to as therapeutic agents.

The injection approach may utilize a catheter like the one described in U.S. Patent Application No. 2005/0070844, "Deflectable Catheter Assembly and Method of Making Same," incorporated herein in its entirety. The catheter may include a distal deflecting portion, which has a needle that may be extended or retracted from its distal tip. Due to the highly dynamic nature (e.g., wall motion) of the beating heart and the difficulties in externally visualizing a catheter placed therein, the stability of the catheter tip with respect to the heart wall may be difficult to determine.

One existing approach used to indicate a successful needle penetration into ventricular tissue is to detect a premature ventricular contraction (PVC) after extending the needle. In other words, this approach assumes that a PVC will be triggered by the needle penetrating the heart wall. This approach is problematic for several reasons. One is that a PVC may occur for a number of reasons besides needle penetration (e.g., stress, caffeine and dehydration may increase the heart's sensitivity/likelihood of producing spontaneous PVC's and typically, excessive mechanical deformation of the heart muscle, such as by a needle or a catheter tip, may produce a PVC), which results in false positives. In other words, a PVC may occur when a needle penetration is attempted, when in fact the needle penetration was unsuccessful and the PVC was triggered by the deformation of the heart muscle as the needle was extended. Another problem is that healthy and ischemic tissue does not always generate a PVC upon needle penetration. Yet another problem is that dead or scar tissue does not generate a PVC. As a result, the region of treatment may receive more damage than it might otherwise (e.g., due to repeated penetrations after a false negative) or not be treated at all (e.g., due to lack of needle penetration).

Generally, a cardiac catheter is used in a catheter lab facility, or cath lab. Such labs are crowded with equipment and people involved in the catheterization procedure, such as physicians, assistants, and, of course, the patient. Information recorded by, for example, electrodes disposed at the distal end of a catheter travels through wires in the catheter out of the patient's body and then, through a wired connection, to a data processing system in order to display the electrode data to the physician, assistant, etc. This multitude of wires further crowds a crowded lab and the sterile work area/the area of the patient near the catheter insertion site which impairs the efficiency of the medical practitioners. FIG. 13 illustrates the wired system. Electrodes 1305 disposed on the distal end of catheter body 1310 transmit data through wires in catheter body 1310 back through handle 1315 outside the patient into an electrical junction 1320. From junction 1320, data travels over a wired connection to data processing system 1325 which displays the electrode data in the form of an ECG. Additionally, if the catheter must be rotated during use (a requirement of a needle injection catheter used to treat a ventricle of the heart), then the wired connections between the catheter handle 1315 and data processing system 1325 will become twisted and possibly fail or become tangled with other cath lab devices, if special care is not taken.

SUMMARY

Determining stability of a catheter is described. A first signal originating from a first region of a patient is monitored and a second signal originating from a second region of the patient is monitored. First components from a recurring interval of the second signal are extracted, where the recurring interval is defined by the first signal. The first components are compared to determine a first similarity value of the first components over time. The first similarity value is compared to a threshold value to determine a stability evaluation for a source of the second signal.

BRIEF DESCRIPTION OF THE DRAWINGS

The present invention is illustrated by way of example and not limitation in the figures of the accompanying drawings in which like references indicate similar elements.

DETAILED DESCRIPTION

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a through understanding of various embodiments of the present invention. However, in certain instances, well-known or conventional details are not described in order to provide a concise discussion of embodiments of the present inventions.

A measurement of stability of the catheter tip against the heart wall may be used to determine a likelihood of success of a subsequent needle extension and therapeutic agent delivery. A high measure of stability indicates that the catheter tip is moving with the heart wall in a repeating manner and is flush against the heart wall, which increases the likelihood that the needle, when extended, will penetrate and seat firmly in the heart wall. By contrast, a low measure of stability indicates that the catheter tip is not moving in a repeating manner with the heart wall, which increases the likelihood that a needle extension will scrape against the wall and/or force the tip of the catheter off of the heart wall rather than penetrating the heart wall and seating firmly. Scraping or bouncing the needle on the heart wall may result in increased damage to the wall by the needle and/or a lack of tissue penetration and injection success.

A measurement of stability of the catheter tip against the heart wall may be used to determine a likelihood of a needle extension having resulted in a successful penetration of the heart wall. If the needle has successfully penetrated the heart wall, it will act as an anchoring point to the catheter tip and increase the measurement of stability. If the needle has not successfully penetrated the heart wall, the tip of the catheter will be forced away from the heart wall and the tip of the needle will act as pivot point, causing the catheter tip to move more and not in as a repeatable a manner as it did prior to needle extension. Thus, if the needle has not successfully penetrated the heart wall, its measurement of stability will decrease. Thus, if an injection has not yet been performed, then an increase in the measurement of stability indicates that performing an injection is more likely to be successful and a decrease in the measurement of stability indicates that performing an injection is less likely to be successful. Alternatively, if an injection has been performed, then an increase in the measurement of stability indicates that the injection was successful and a decrease in the measurement of stability indicates that the injection was not successful.

Figure 1A:
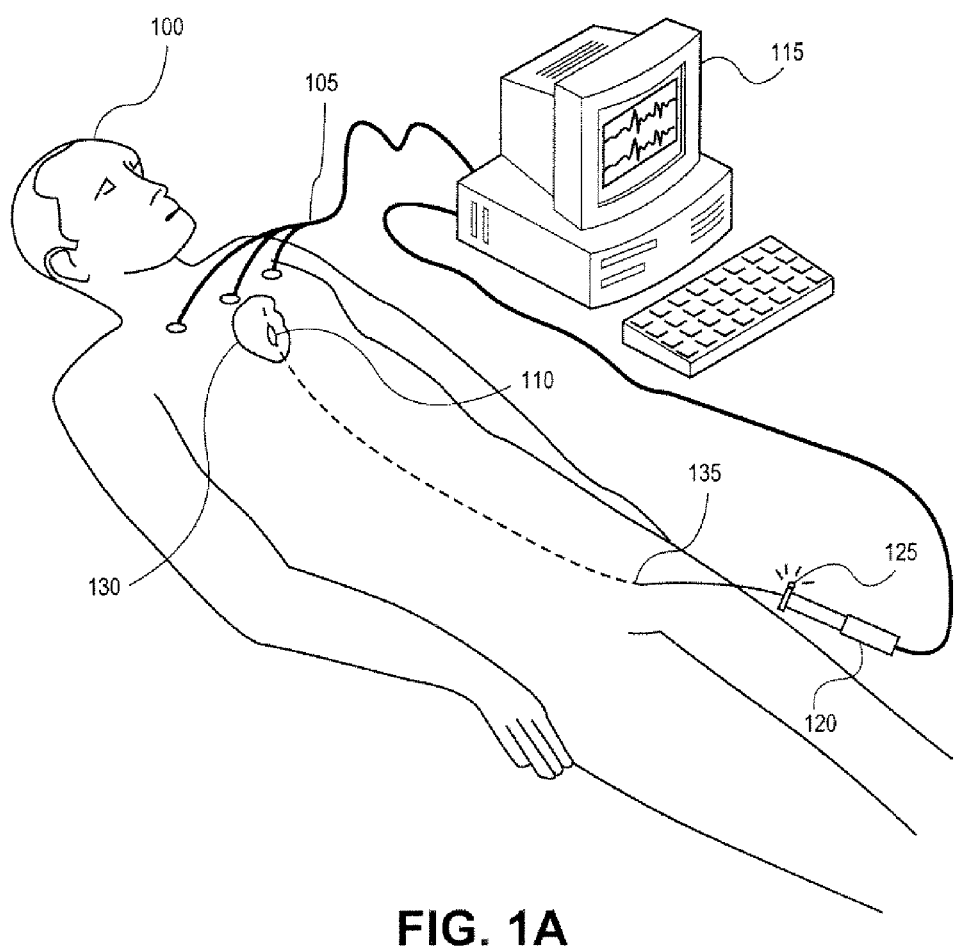
FIG. 1A is a diagram illustrating a patient and a system suitable for operation of an embodiment of the invention.

FIG. 1A is a diagram illustrating a patient and a system suitable for operation of an embodiment of the invention. Surface electrodes 105 are fixed to the exterior of patient 100 (e.g., on the chest) and are electrically coupled to computer 115. FIG. 1A depicts an embodiment using three surface electrodes. Other embodiments may use other numbers and/or other placements of electrodes. Catheter 110 is introduced through femoral artery 135 and navigated to heart 130 of patient 100. Catheter 110 contains electrodes electrically coupled to computer 115. Catheter handle 120 remains outside of patient 100 and allows a medical practitioner (not shown) to navigate catheter 110. Indicator 125 may be located on handle 120 and provides an indication of catheter stability, needle penetration success, etc., based on measurements determined by computer 115 using electrode data from electrodes coupled to catheter 110 and surface electrodes 105.

In one embodiment of the invention, computer 115 uses a primary signal received by a surface electrocardiogram (e.g., surface electrodes 105) as a gating signal for extracting and comparing components of a secondary signal received by electrodes (e.g., electrodes coupled to catheter 110) disposed within a heart chamber (e.g., the left ventricle of heart 110) and mounted near a distal tip of the catheter. Computer 115 may use a comparison of consecutive components of the secondary signal from adjacent cardiac cycles to determine whether or not the intracardiac electrodes are physically stable.

Physical stability may be defined as the condition where there is little change in the motion of the electrodes relative to the ventricular wall during the cardiac cycle. In other words, any motion of the catheter's electrodes relative to the ventricular wall is cyclically repeatable in time with the cardiac cycle. Computer 115 may use stability of the intracardiac electrodes to provide an indication of the stability of a catheter coupled to the electrodes. Catheter stability is described in greater detail below in conjunction with FIG. 3. Computer 115 may also use changes in correlation coefficients derived from this comparison to determine whether stability has increased or decreased in response to a procedural step or steps. Changes in catheter stability resulting from procedural steps is described in greater detail below in conjunction with FIG. 12.

Figure 1B:
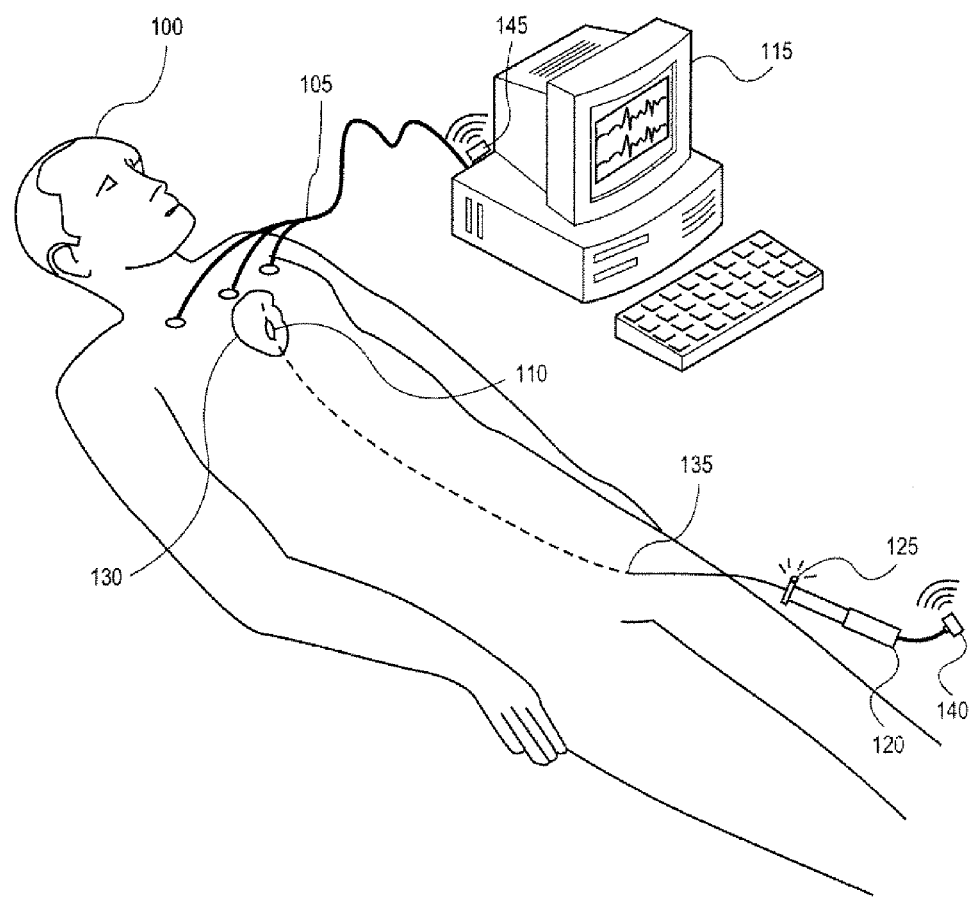
FIG. 1B is a diagram illustrating a patient and a system suitable for operation of another embodiment of the invention.

FIG. 1B is a diagram illustrating a patient and a system suitable for operation of another embodiment of the invention. Wireless transceivers 140 and 145 may be used to allow wireless communication between catheter 110 and computer 115. Wireless catheter communication is described in greater detail below in conjunction with FIGS. 14 and 15. In other embodiments, surface electrodes 105 may be wirelessly coupled to computer 115.

Figure 2:
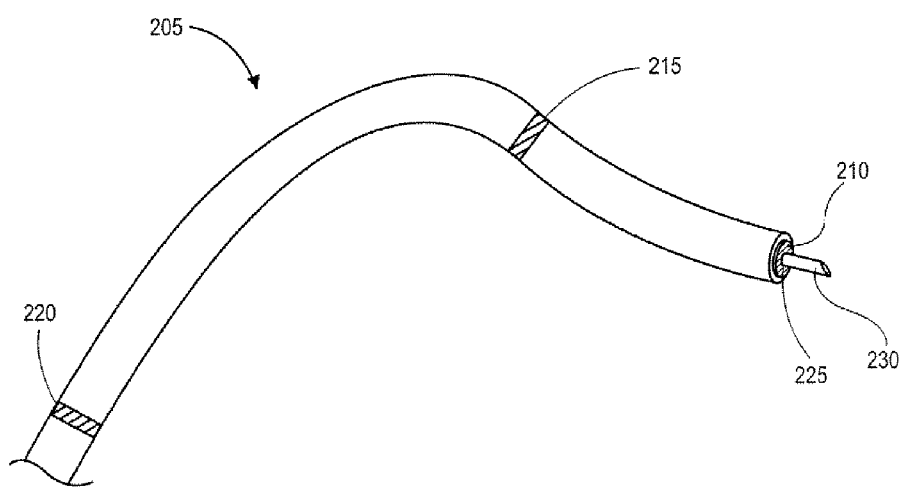
FIG. 2 is a diagram illustrating a catheter suitable for use with an embodiment of the invention.

FIG. 2 is a diagram illustrating a catheter suitable for use with an embodiment of the invention. Catheter 205 is coupled to tip electrode 210, distal electrode 215, and reference electrode 220. Reference electrode 220 is preferably coupled to the catheter 205 such that when the tip electrode 210 and the distal electrode 215 are within the electrical field of the ventricular chamber, the reference electrode 220 is located outside of the field. Catheter 205 also includes needle port 225 through which needle 230 may be extended. It is preferred that tip electrode 210 be electrically insulated from a needle 230 that is constructed of a conductive material (like stainless steel) or that needle 230 be constructed of a non-conductive material, such as ceramic. Electrodes 210, 215, and 220 may be electrically coupled to an external system, such as computer 115. Catheter 205 is coupled to a catheter handle, such as catheter handle 120 (illustrated in FIG. 1), which a medical practitioner (not shown) may use to guide and position the catheter to regions of the heart which may require treatment (e.g., ischemic regions within the left ventricle). When needle port 225 is in contact with the wall of the heart and stable with respect to the wall of the heart, needle 230 may be extended into the wall of the heart, and a therapeutic agent injected (e.g., stem cells, etc.)

Figure 3:
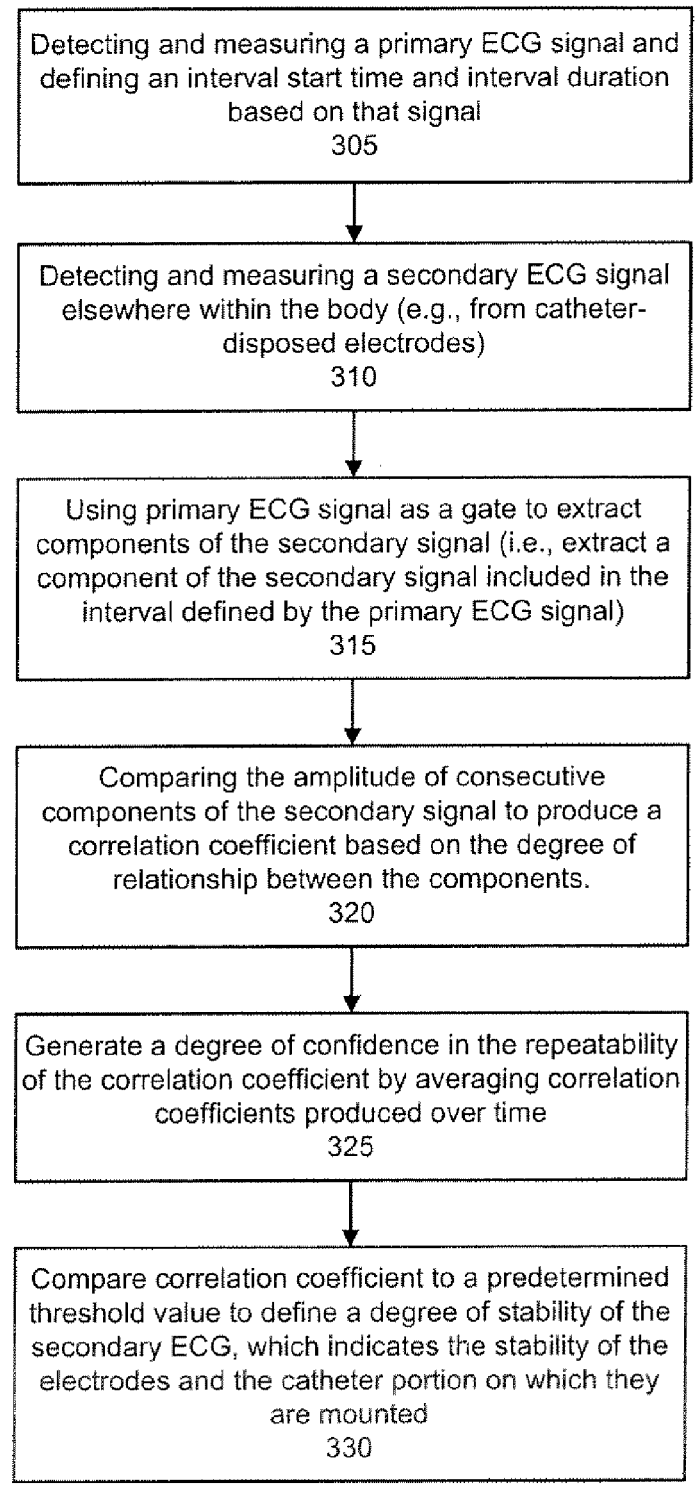
FIG. 3 illustrates a method of determining catheter stability according to an embodiment of the invention.

FIG. 3 illustrates a method of determining catheter stability according to an embodiment of the invention. In one embodiment, a data processing system such as computer 115 may perform the method. At block 305, the method detects and measures a primary ECG (electrocardiograph) signal. An electrode on the surface of a patient, such as surface electrodes 105, may provide data for the primary signal. The method uses the primary signal to define an interval start time and an interval duration. Defining intervals is described in greater detail below in conjunction with FIGS. 5A-5C.

At block 310, the method detects and measures a secondary ECG signal from elsewhere within the body of the patient. For example, electrodes disposed on a catheter, such as catheter 200, may provide data for the secondary signal. Detecting and measuring a secondary signal is described in greater detail below in conjunction with FIG. 8.

At block 315, the method uses the primary signal as a gate to extract components of the secondary signal. A component of the secondary signal is defined as a subset of the secondary signal over time. The beginning of the component is specified by the interval start time, and the length of the component is specified by the interval duration. Extracting components of the secondary signal is described in greater detail below in conjunction with FIG. 8. The primary signal originates from the surface of the patient and provides an "average" of the electrical activity of the cardiac cycle. The electrodes providing the secondary signal measure a more localized portion of the electrical activity. Extracting components of the secondary signal based on an interval defined by the primary signal therefore provides a relatively stable frame of reference against which to compare components of the secondary signal extracted over time.

At block 320, the method compares the amplitude of consecutive components of the secondary signal to produce a correlation coefficient based on the degree of relationship between the components. At block 325, the method generates a degree of confidence in the repeatability of the correlation coefficient by averaging correlation coefficients produced over time. Correlation coefficients and degrees of confidence are described in greater detail below in conjunction with FIGS. 9 and 10.

At block 330, the method compares correlation coefficients to a predetermined threshold value to define a degree of stability of the secondary ECG signal, which indicates the stability of the electrodes and the stability of the catheter portion upon which the electrodes are disposed. Defining a degree of stability is described in greater detail below in conjunction with FIG. 11.

Figure 4A:
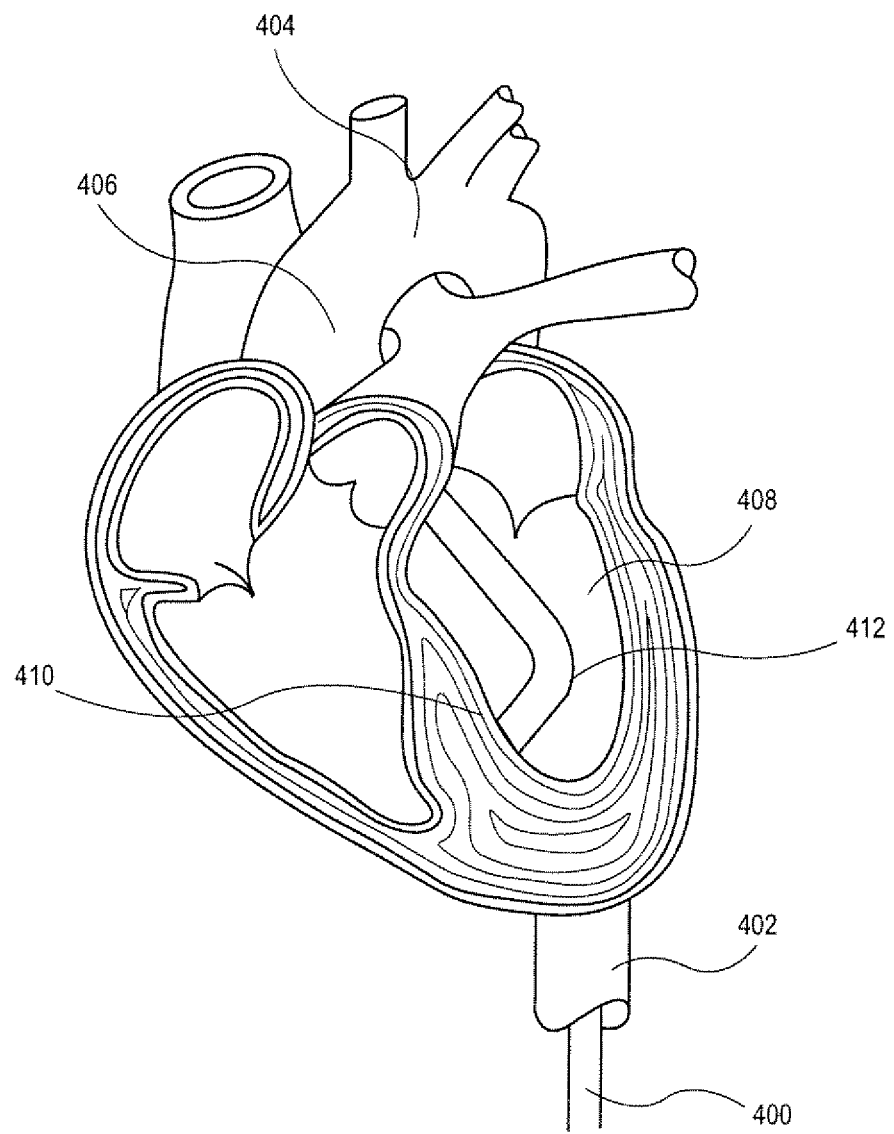
FIGS. 4A-4D are diagrams illustrating various configurations of a heart and a catheter according to embodiments of the invention.

FIGS. 4A-4D are diagrams illustrating various configurations of a heart and a catheter according to embodiments of the invention. FIG. 4A illustrates catheter 400 entering the patient through the femoral artery in the groin region (not shown) through an access path created by a percutanteously placed introducer sheath as is well known in the art. The catheter 400 travels into the descending aorta artery 402, over the aortic arch 404, down the ascending aorta 406, across the aortic valve (not shown) and into the left ventricle 408. Catheter tip 412 is positioned over treatment region 410. In the instance of time illustrated by FIG. 4A, catheter tip 412 is stable against treatment region 410 and may be stable enough for a needle extension. Stability is described greater detail below in conjunction with FIGS. 9 and 10.

Figure 4B:
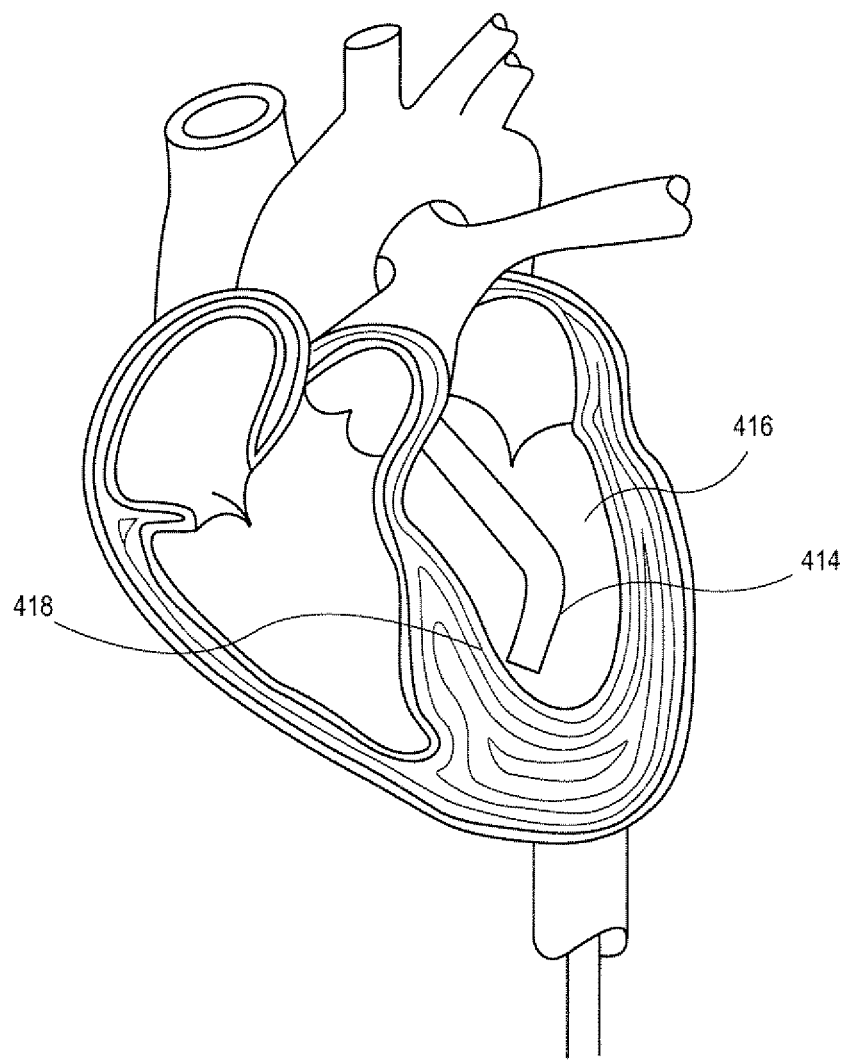
Figure 4C:
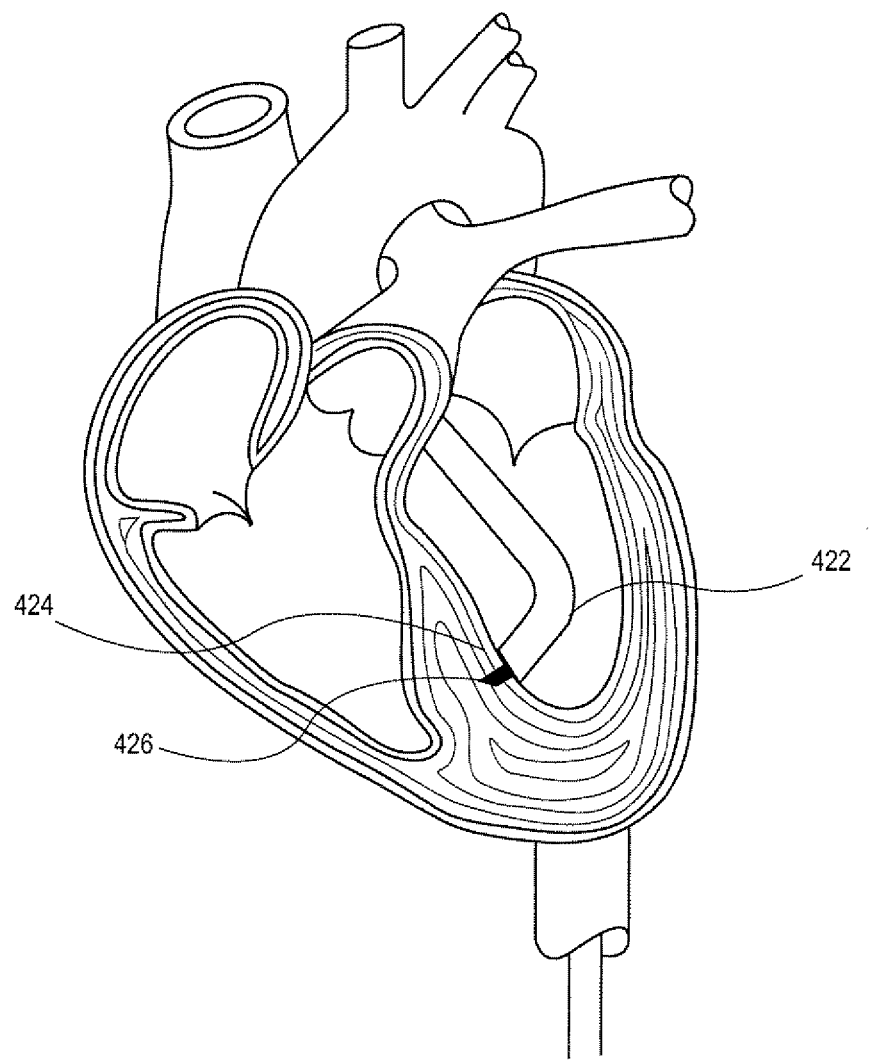
Figure 4D:
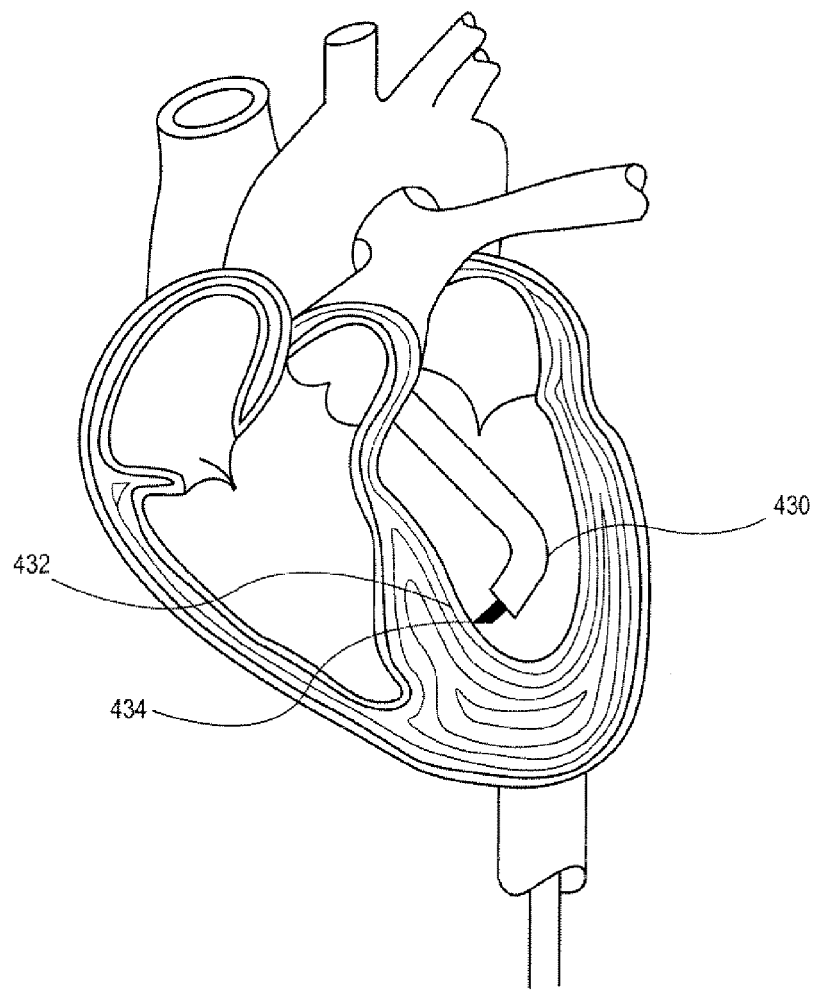

FIG. 4B illustrates the situation where catheter tip 414 is in left ventricle 416 but is not stable against treatment region 418. As described in greater detail below in conjunction with FIG. 10, catheter tip 414 may not be stable enough to risk a needle extension. FIG. 4C illustrates the situation where, following the indication of stability illustrated in FIG. 4A, needle 426 is extended from catheter tip 422 and successfully penetrates treatment region 424. As described in greater detail below in conjunction with FIG. 12, a prediction of penetration success may be proper, and injection of a therapeutic agent may now proceed. FIG. 4D illustrates the situation where, following the indication of stability illustrated in FIG. 4A, needle 434 is extended from catheter tip 430 and does not penetrate treatment region 432. Rather, the extended needle has moved catheter tip 430 farther away from the treatment region, and may cause a decrease in catheter stability as described below in greater detail in conjunction with FIG. 12.

Figure 5A:
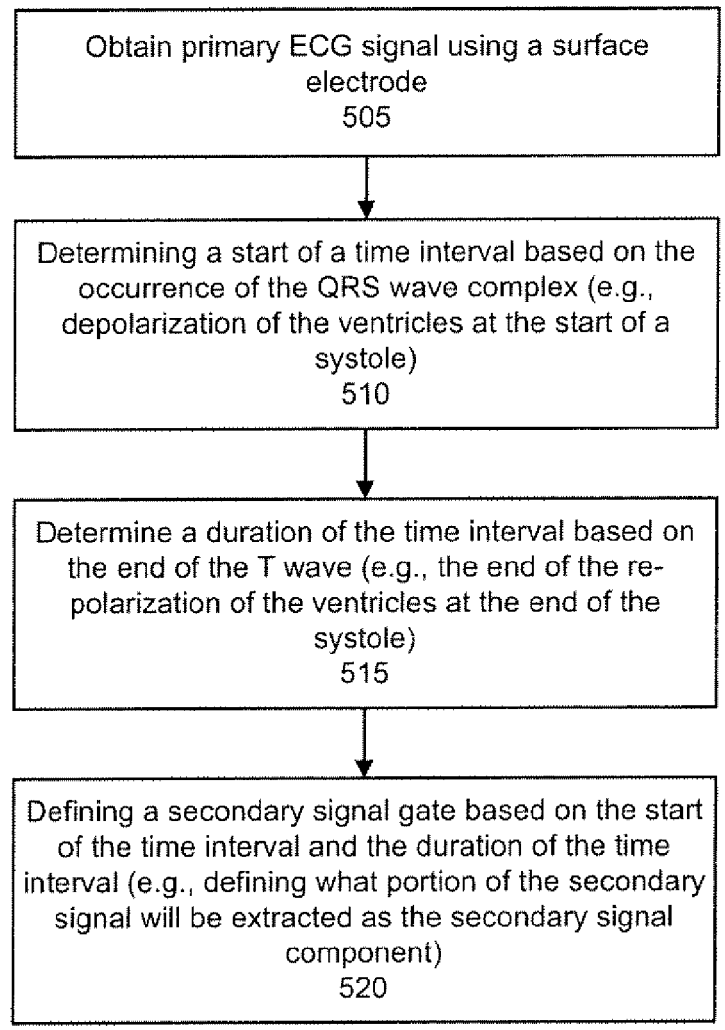
FIG. 5A illustrates a method for detecting and measuring a primary ECG signal and defining an interval start time and interval duration based on that signal according to an embodiment of the invention.

FIG. 5A illustrates a method for detecting and measuring a primary ECG signal and defining an interval start time and an interval duration based on that signal according to an embodiment of the invention. At block 505, the method obtains a primary ECG signal using a surface electrode. For example, an electrode or electrodes may be affixed to the patient's chest and connected to a data processing system such as computer 115. At block 510, the method determines the interval start time based on the occurrence of the QRS wave complex, known in the art as R-wave gating. In other words, the beginning of the time interval is approximately linked to the depolarization of the ventricles at the start of a systole.

At block 515, the method determines a duration of the time interval based on the end of the T wave. In other words, the end of the time interval is approximately the end of the repolarization of the ventricles at the end of the systole. In one embodiment, several cardiac cycles recorded by the surface ECG are averaged to produce a smoother waveform upon which the interval duration is based. In one embodiment, the interval duration is fixed after block 515. In other words, the gate depends upon the occurrence of the QRS wave complex to begin each interval, but the end of each interval is defined by the start plus the duration, not the actual occurrence of the end of the T wave. At block 520, the method defines a secondary signal gate based on the start of the time interval and the duration of the time interval. This signal gate defines the extracted components of the secondary ECG signal.

Figure 5B:
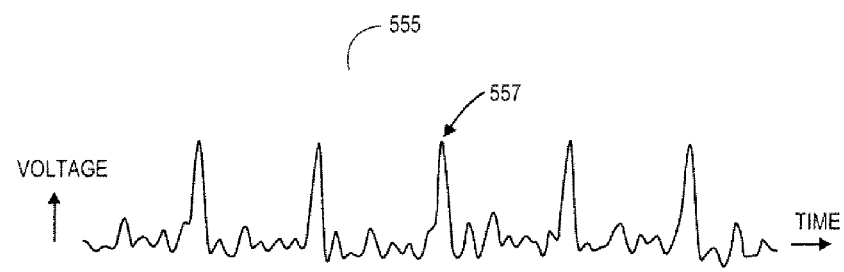
FIGS. 5B and 5C show ECG signals which may be used in at least certain embodiments of the invention.

FIG. 5B is a diagram illustrating an example of a surface ECG which an embodiment of the invention may use to create a secondary signal gate. In a clinical environment, a surface ECG may contain noise, which is represented in FIG. 5B. Even in a noisy ECG, however, the R wave is readily identifiable, as indicated by wave peak 557. The vertical axis represents voltage and the horizontal axis represents time. Waveform 555 may be averaged to remove noise using R wave gating of several cardiac cycles, as illustrated in greater detail in FIG. 5C. Wave peak 560 corresponds to the peak of the R-wave, and may define the beginning of gating interval 570, which represents the latter half of the QRS wave complex. In other embodiments, the type of R-wave gating employed may define another repeatable position on the QRS wave complex as the beginning of the gating interval 570. A fixed position on the QRS wave complex defines the presently preferred beginning of the gating interval 570 for ventricular applications. The end of T-wave 565 defines the presently preferred end of the gating interval for ventricular applications.

Figure 5C:
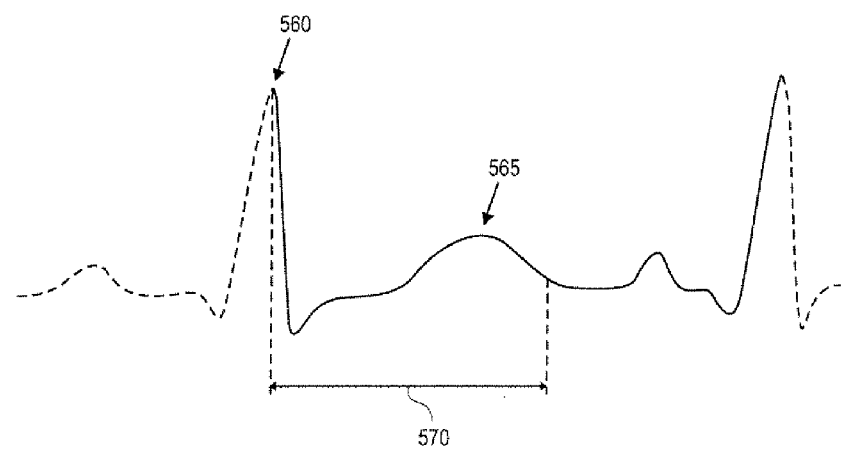

This R/T interval is presently preferred for ventricular applications because, during this interval of the cardiac cycle, the most violent motion of the heart wall occurs and thus, provides an enhanced opportunity to detect potential position instability is during this interval. In some embodiments, several noisy surface ECG's may be averaged together to produce a smoother ECG as illustrated in FIG. 5C. A smoother ECG may allow automatic identification of the T wave, which permits gating based on the interval defined by the R and T waves. Such identification may occur by eye (e.g., practitioner viewing an ECG trace/waveform and moving a cursor to indicate the end of the T wave) or by a computer such as computer 115 using signal gating and/or other conventional methods of waveform analysis.

It is also presently preferred because, during the R/T interval, the depolarization/repolarization waves travel through/across the ventricular walls, creating the largest change in the voltage field inside of the ventricle which is detected via the catheter electrodes and provides a high amplitude and changing waveform, which is the most suitable for analysis. In one embodiment, this system uses a cardiac catheter which may be placed within the left ventricle, so the most relevant electrode data will be gathered during the depolarization/re-polarization of the ventricles. The R/T wave gating interval captures this relevant data.

In another embodiment, such as device or catheter positioning and measurement of position stability in the atria, the interval beginning at the start of the P-wave and ending at the R-wave, at the beginning of the T-wave or at the end of the T-wave may be the most relevant gating interval. In more complex embodiments making more sophisticated use of the memory of computer 115, the beginning and/or end of the gating interval may be a specified or computed time before or after the detected event (for instance, 20 milliseconds before R-wave detection as the start of a ventricular interval, the end of the interval is the end of the T-wave plus 10% of the R-wave to R-wave interval, etc.).

Such modifications of the interval beginning and/or stop times are anticipated to be beneficial in ensuring that the desired portions of the cardiac cycle are included and the undesired portions are excluded, regardless of which waveform detection algorithms are used and/or which waveform detection algorithms prove to be the most reliable. For instance, in a ventricular application, beginning the gating interval a short time prior to the detection of the primary signal R-wave peak can ensure that the rapidly changing depolarization secondary waveform is within the gating interval, regardless of the catheter's position on the ventricular wall.

Returning to FIG. 2, tip electrode 210, distal electrode 215, and reference electrode 220 are disposed on catheter 205. Only two electrodes are required to produce an intracardiac ECG. However, modern ECG monitoring circuitry requires a third, reference input. Tip electrode 210 and distal electrode 215 receive electrical signals from the anatomy, and those signals are compared to produce the bipolar electrode intracardiac ECG as is known in the art, while the reference electrode is used as the reference input to the ECG monitor. In one embodiment, the ECG monitor is a data processing system such as computer 115. Other reference inputs are possible, but the bipolar ECG with this reference results in the least intracardiac ECG signal noise and doesn't require another electrode on another catheter to be positioned near the heart. The bipolar ECG is bipolar in the sense that both of the sensing electrodes are positioned inside of the electrical field of the ventricular chamber.

In another embodiment, a unipolar electrode connection to the ECG monitor may be used. For example, catheter 205 may be used to obtain a unipolar electrode connection by comparing either the tip or distal electrode signal with the reference electrode signal and using the remaining electrode to connect to the ECG monitor's reference input. This ECG signal is unipolar in the sense that only one of the sensing electrodes is positioned inside the electrical field of the ventricular chamber. A unipolar design is less sensitive than a bipolar design for measuring the secondary ECG signal because only the voltage variations of one portion of the catheter (i.e., where the tip electrode or distal electrode is disposed on the catheter) are detected. Unlike the unipolar configuration, the reference electrode in the bipolar configuration is outside of the electric field of the ventricular chamber and not subject to the large signal changes in response to motion of the catheter's tip. Thus, the bipolar electrode design is the preferred embodiment.

When comparing two waveforms for similarity in one embodiment, the same number of recorded amplitudes after the beginning of gating interval 570 may be used, one from each waveform, to create (x,y) data points (for example, all "x" values are from one waveform and all "y" values are from the other waveform) for a regression analysis. In one embodiment, the same gating interval duration and data sampling rate is used for all secondary ECG waveforms to be analyzed for a stability determination. In another embodiment, the data points that fit into the minimum gating interval at the same data sampling rate are used to collect the two waveforms to be analyzed for a stability determination. A preferred embodiment uses the same gating interval and data sampling rate for all secondary ECG waveforms to be analyzed for a stability determination. This embodiment is preferred because it reduces a dependence of the correlation coefficient on the number of data points used and provides a slight increase in precision when averaging correlation coefficients from substantially identical portions of the cardiac cycle.

Figure 6:
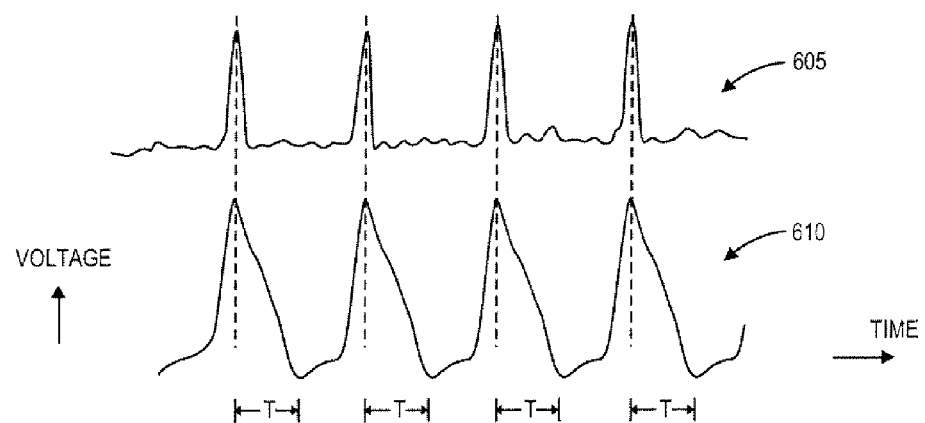
FIG. 6 is a diagram illustrating a primary ECG signal and a secondary ECG signal according to an embodiment of the invention.

FIG. 6 is a diagram illustrating a primary ECG 605 (i.e., a surface ECG) and a secondary ECG 610 (i.e., a catheter intracardiac ECG) according to an embodiment of the invention. The catheter ECG shows the most stability-significant activity during the depolarization/re-polarization portion of the surface ECG. When the catheter electrodes are stable, the catheter ECG waveform will have substantially the same amplitude and timing relative to the surface ECG for each cardiac cycle. If a catheter electrode shifts its position within the ventricular chamber relative to its position at the same time in the previous cardiac cycle, or becomes disengaged from the heart wall, the catheter ECG waveform will change with respect to the timing of the surfaced ECG trace.

Figure 7:
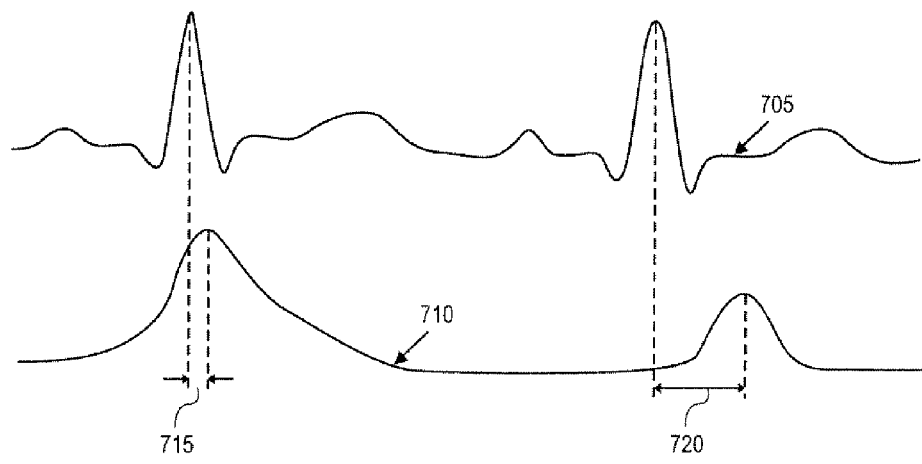
FIG. 7 is another diagram illustrating a primary ECG signal and a secondary ECG signal according to an embodiment of the invention.

FIG. 7 is a diagram illustrating a primary ECG 705 and a secondary ECG 710 according to an embodiment of the invention. Offset 715 represents the R wave depolarization offset between primary signal 705 and secondary signal 710 during a cardiac cycle. Offset 720 represents the R wave or depolarization offset between primary signal 705 and secondary signal 710 during a subsequent cardiac cycle. The variation in the secondary signal 710 between cycles indicates that the electrodes generating the secondary signal are not in the same position relative to the position of the electrodes in the earlier cardiac cycle. In other words, the electrodes and the catheter upon which they are mounted are not stable, as may be seen in FIG. 4B. Additionally, it should be noted that the voltage levels of the secondary signals are different at the same positions in time after the peak of the R-wave in the primary signal (at the same time in the cardiac cycle). This also is an indication that the catheter is not stable The beating of the heart occurs rapidly and powerfully. The resulting tissue contractions will move the catheter and its electrodes within the ventricle. The electrical field inside the ventricle changes with time and with position inside the chamber. However, at any particular position inside the chamber, the electric field repeats its changes very consistently from cardiac cycle to cardiac cycle. When the catheter is unstable, the electrodes will move to different positions inside the chamber at different times during the cardiac cycle. As a result, the catheter's ECG trace will shift and change significantly from cardiac cycle to cardiac cycle. In contrast, when the catheter is stable, the catheter electrodes will repeatedly move to the same positions within the chamber from cardiac cycle to cardiac cycle and the catheter's ECG trace/waveform will appear more consistent over time in relation to the surface ECG trace, which provides the timing reference from cardiac cycle to cardiac cycle.

Visual analysis of a continuous catheter ECG alone is inadequate to determine whether shifts and changes of the traces along the time axis are significant enough to indicate catheter instability. Reliable analysis of the catheter ECG with regard to stability is improved if the analysis compares the waves at the same time points in the cardiac cycle.

Figure 8:
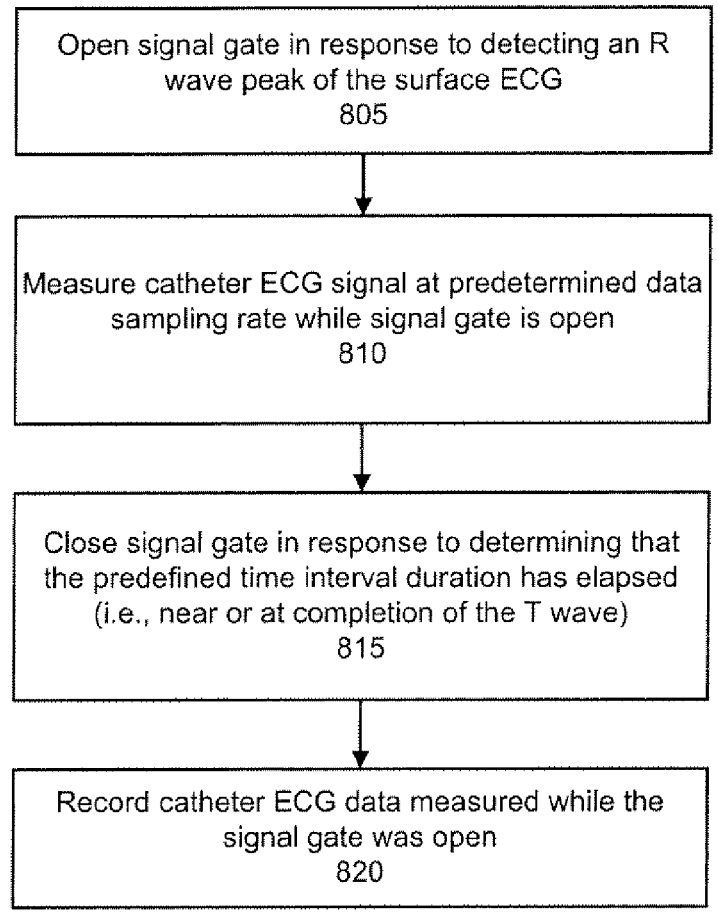
FIG. 8 illustrates a method of using the primary ECG signal as a gate to extract components of the secondary data according to an embodiment of the invention.

FIG. 8 illustrates a method of using the primary ECG signal as a gate to extract components of the secondary data according to an embodiment of the invention. At block 805, the method opens a signal gate in response to detecting an R wave peak of the surface ECG. An example of an R wave peak in the surface ECG may be seen wave peak 560 at the beginning of gating interval 570 in FIG. 5C. At block 810, the method measures the catheter ECG signal at a predetermined sampling rate while the signal gate is open. The catheter ECG signal may be measured continuously at a desired constant or repeating data sampling rate. The measuring of the catheter ECG signal continues until, at block 815, the method closes the signal gate in response to determining that the predefined time interval duration has elapsed. An example of the time interval duration is interval 570 in FIG. 5C. At block 820, the method records catheter ECG data measured while the signal gate was open. The data is saved (recorded) as catheter ECG waveform data. Subsequent cardiac cycles will produce additional catheter ECG waveform data.

Figure 9:
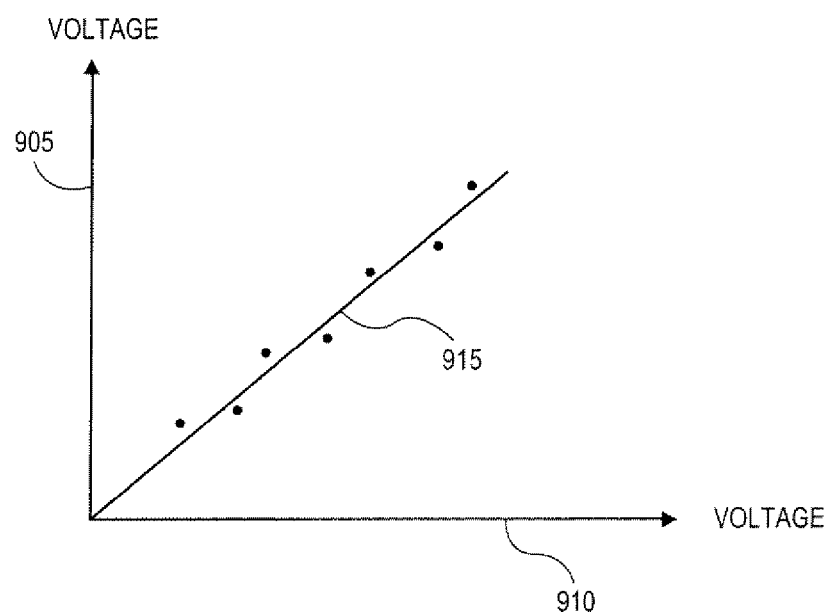
FIG. 9 illustrates an example of a correlation coefficient using data from two catheter waveforms indicating stability according to an embodiment of the invention.

In one embodiment, a linear correlation coefficient may be determined using pairs of recorded catheter ECG waveform data. FIG. 9 illustrates an example of a correlation coefficient using data from catheter waveforms 905 and 910. Amplitude data collected at the same times in the cardiac cycle from the two waveforms are plotted on the graph as (x,y) data points, as previously described. Line 915 represents a linear regression of the various data points. If there was no difference between waveforms 905 and 910, the slope of this line would be 1.00. The line would intercept the x and y axes at zero (0) and all the data points would coincide with the line.

Additionally, the correlation coefficient would be highest possible correlation coefficient, which is 1.0 (i.e., the two waveforms are identical). Thus, the correlation coefficient in this example is quite high, because the data points lie quite close to the line. Additionally, the slope of the line is very near 1 and the line crosses the x and y axes at very near zero (0). All of these calculations are well known in mathematics and indicate that the catheter ECG signals during waveform 905 and waveform 910 are quite similar. This indicates that the catheter electrodes (and thus the distal end of the catheter) were in similar positions at similar times during cardiac cycle 2 (when waveform 910 was recorded) as they were during cardiac cycle 1 (when waveform 905 was recorded). However, the preferred indicative measurement of the similarity of the two waveforms 905 and 910 is the correlation coefficient.

If the catheter electrodes undergo some minimal motion from heartbeat to heartbeat, but are in relatively fixed or repeatable positions in the ventricle, the graph and regression analysis of the data points may look like the graph illustrated in FIG. 9. The minimal motion of the catheter could be due to the tip electrode being engaged with an indentation in the myocardial wall (e.g., trabeculae) and/or the tip being held by sufficient force from the catheter to remain engaged (touching/pushing) with the wall of the heart while the distal electrode consistently rocks back and forth with the beating of the heart. This supports a prediction that the distal portion of the catheter is in a stable position. As is known in the art, because the ECG generated by the heart has some minimal variation from cardiac cycle to cardiac cycle, some catheter ECG variation between cardiac cycles will occur.

Figure 10:
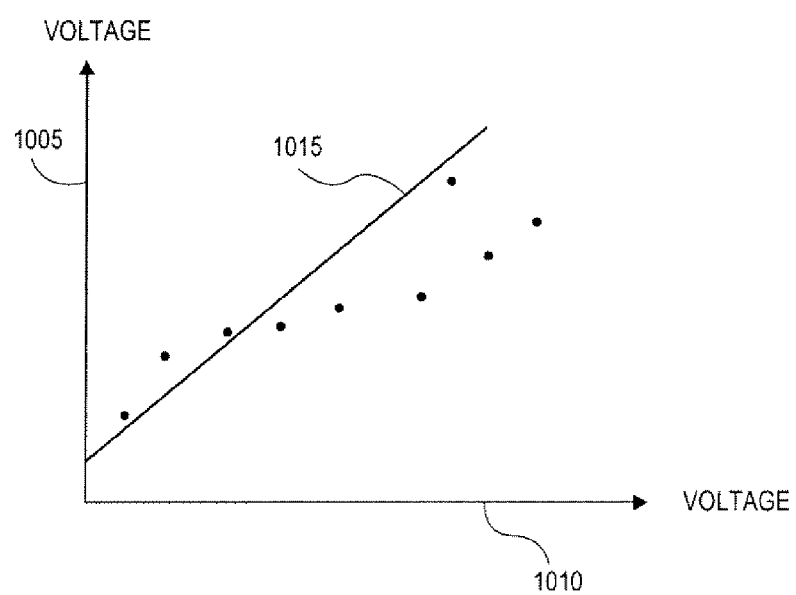
FIG. 10 illustrates an example of two catheter waveforms whose correlation coefficient indicates a lack of stability according to an embodiment of the invention.

Alternatively, FIG. 10 illustrates an example of two catheter waveforms whose correlation coefficient indicates a lack of stability. Waveform 1005 and waveform 1010 result in line 1015 which possesses a correlation coefficient of 0.70, due to the variation in catheter ECG between the two waveforms relative to the surface ECG (at the same times in the cardiac cycle). The low correlation coefficient between the two waveforms indicates that the catheter electrodes have shifted significantly within the chamber and the electrical signals sensed by the electrodes are being sensed from different positions within the ventricle during the open signal gate from cardiac cycle to cardiac cycle. This supports a prediction that the tip of the catheter is not stable against the wall of the heart.

Since some variation in catheter ECG waveforms is expected, there is a need to produce correlation coefficients for more than two consecutive catheter ECG waveforms once the stability of the catheter tip needs to be evaluated. The number of waveforms that should be compared depends on the degree of confidence and reliability required. In the preferred embodiment, based on animal testing, an average of ten successive catheter ECG trace comparisons produces an average correlation coefficient that is reliable and may be generated in a reasonable period of time (usually less than ten seconds).

Figure 11:
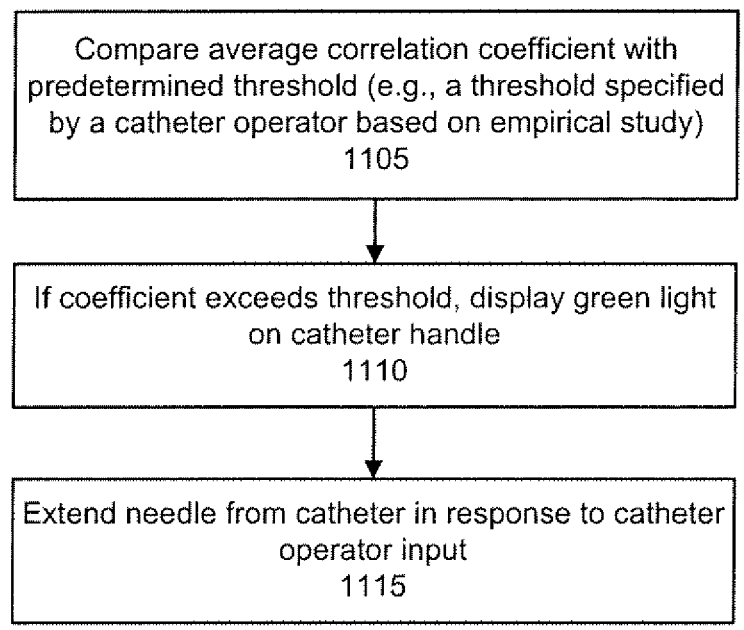
FIG. 11 illustrates a method for extending the catheter needle in response to determining the catheter tip is stable according to an embodiment of the invention.

FIG. 11 illustrates a method for extending the catheter needle in response to determining the catheter tip is stable according to an embodiment of the invention. At block 1105, the method compares the average correlation coefficient of a series of catheter ECG waveforms with a predetermined threshold. In one embodiment, a data processing system such as computer 115 may compare the average correlation coefficient to a threshold and produce an output based on the comparison (e.g., a command to display a green light). At block 1110, the method causes light 125 on catheter handle 120 in FIG. 1 to illuminate a green light if the coefficient exceeds the threshold. In one embodiment, if the coefficient is less than the threshold, the method causes light 125 to illuminate a red light. If light 125 is green, the catheter operator may combine that stability indicator with a view of the catheter image on a fluoroscope or other imaging modality to determine that the catheter tip is engaged with the myocardial tissue at an appropriate location. At block 1115, the method extends the needle in response to catheter operator input. In healthy and infarcted pigs, a ten cycle average coefficient of 0.98 or greater indicates sufficient stability for a needle extension.

Figure 12:
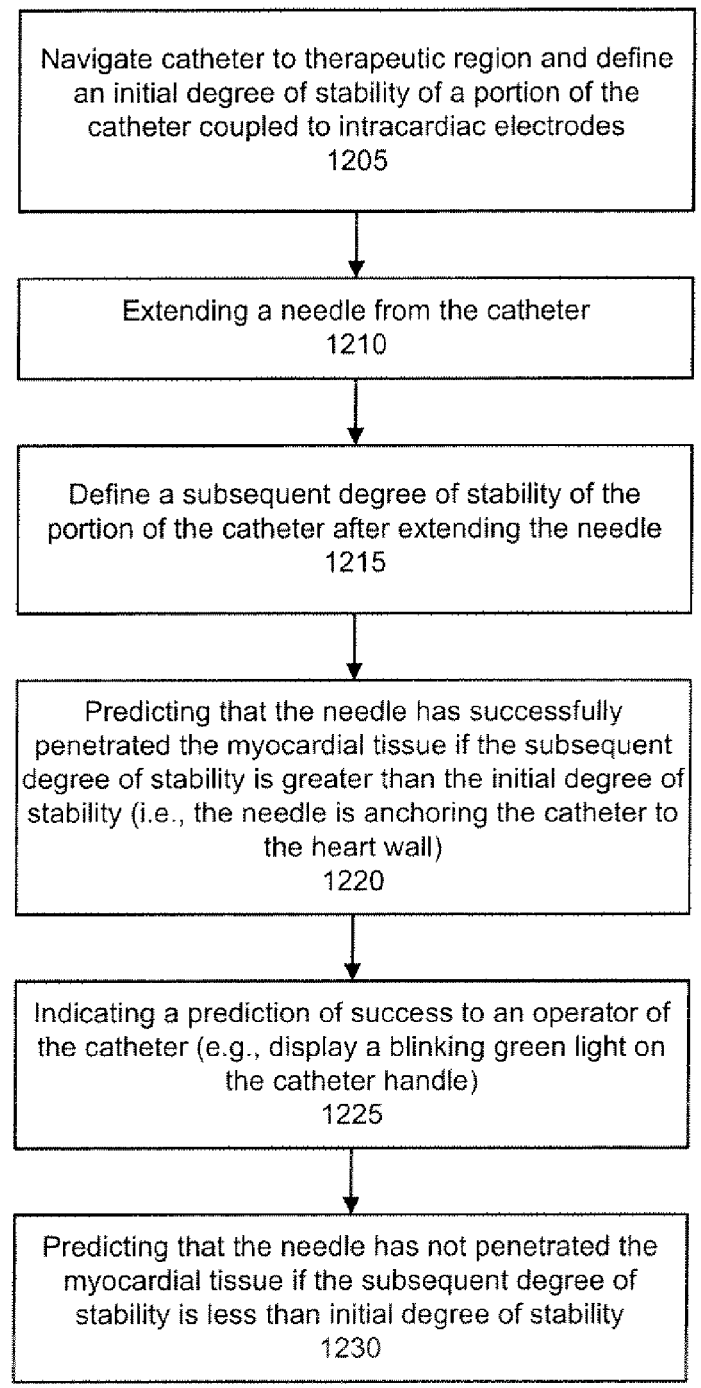
FIG. 12 illustrates a method of determining a change in stability according to an embodiment of the invention.
Figure 13:
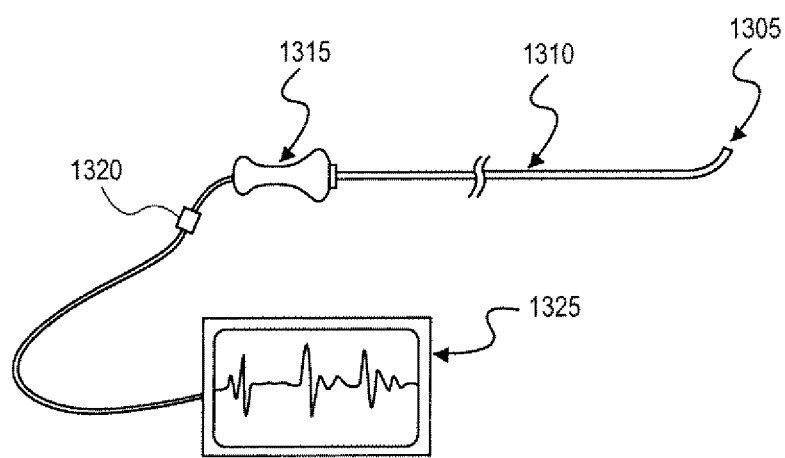
FIG. 13 illustrates a prior art system of a wired connection between a catheter and a data processing system.

FIG. 12 illustrates a method of determining a change in stability according to an embodiment of the invention. The method illustrated in FIG. 12 may be executed by a catheter operator in conjunction with a data processing system such as computer 115. At block 1205, a catheter is navigated to a treatment region (e.g., wall of the heart) and an initial degree of stability of a portion of the catheter is determined. In one embodiment, the method illustrated in FIG. 3 may be used to determine the initial degree of stability. At block 1210, if the degree of stability produces a prediction of success, a needle is extended from the tip of the catheter. At block 1215, the method defines a subsequent degree of stability of the portion of the catheter after extending the needle, using, for example, the method illustrated in FIG. 3. If the stability of the catheter has increased following procedural step (e.g., extending the needle), the method at block 1220 predicts that the needle has successfully penetrated the treatment region. In other words, the needle has penetrated the wall of the heart and is functioning as an anchor for the catheter, increasing the degree of stability, such as in FIG. 4C.

At block 1225, the method indicates a prediction of success to an operator of the catheter. The method may, for example, change the steady green light displayed at block 1110 of FIG. 11 to a blinking green light indicating a prediction of penetration success. In another embodiment, a third color, such as blue, may be displayed. In other embodiments, other visual, audio, or tactile indications may be used. At block 1230, the method predicts that the needle has not penetrated the treatment region (e.g., the myocardial/heart wall) if the degree of stability has decreased following the procedural step. In other words, the needle did not penetrate the heart wall, and may be scraping over the surface or repeatedly puncturing the surface at different locations, such as in FIG. 4D.

Empirical data derived from healthy and infarcted swine indicate that successful needle penetration of the ventricular wall is predicted more accurately using a method such as the method illustrated in FIG. 12 than by using conventional PVC indication. Further, the predictive value of this method is retained when injecting into infarcted tissue, since the predictive value is associated with the stability of the catheter, which is unrelated to the electrical characteristics of the penetrated flesh (i.e., dead or scar cardiac tissue does not generate PVCs).

Figure 14:
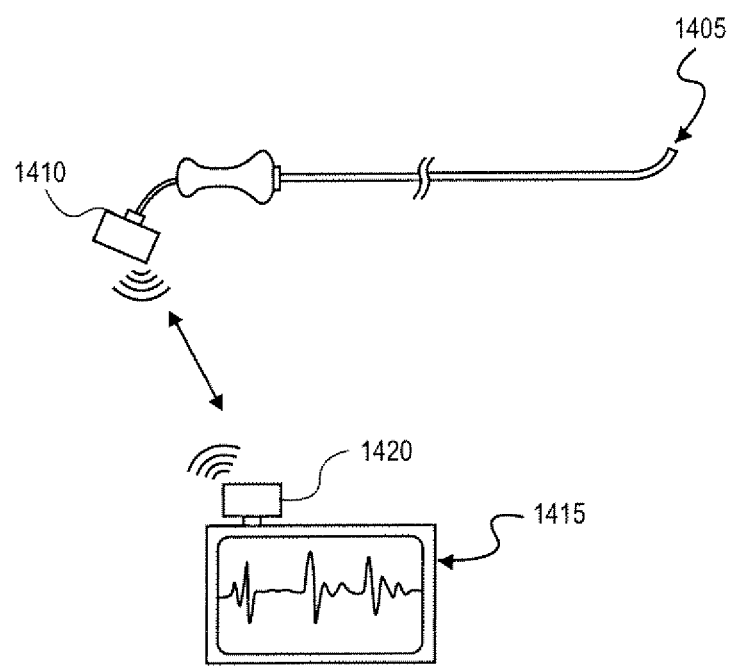
FIG. 14 illustrates a system of wireless connection between a catheter and a data processing system according to an embodiment of the invention.

FIG. 14 is a diagram illustrating wireless catheter communication according to an embodiment of the invention. Electrodes 1405 transmit data through a wired connection in the catheter body to wireless module 1410. Module 1410 transfers data received from electrodes 1405 wirelessly to wireless module 1420, which is coupled to data processing system 1415, which processes and displays the data. In preferred embodiments, module 1410 may be plugged into either a connector on the electrode lead wire cable or into the handle of the catheter, is re-usable and is recharged between uses. In one embodiment, wireless transmission uses a wavelength designated by the Federal Communications Commission for wireless medical telemetry. However, other wireless frequencies may be used.

Figure 15:
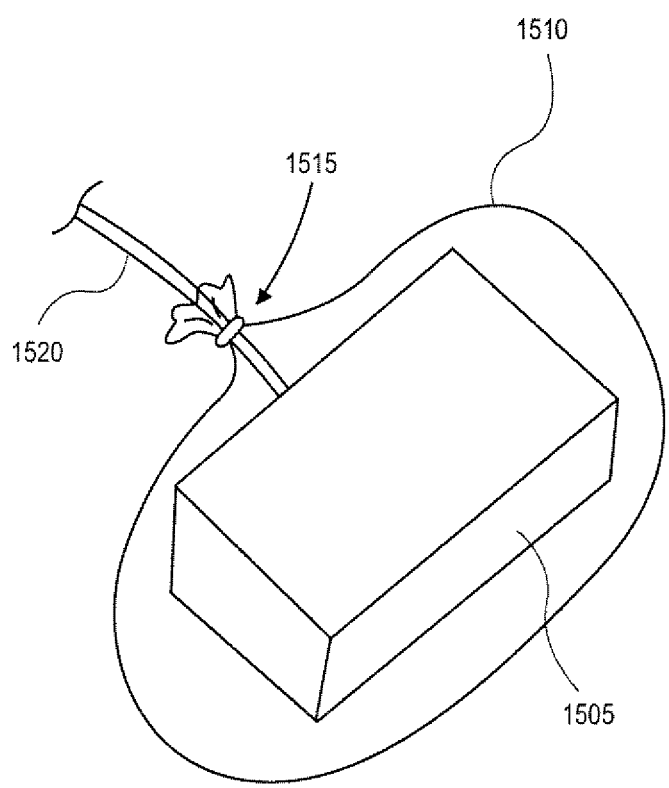
FIG. 15 is a diagram illustrating a wireless catheter module according to an embodiment of the invention.

FIG. 15 is a diagram illustrating a wireless catheter module. Module 1505 is placed in sterile bag 1510 which is sealed using tie-off 1515 around lead 1520 to allow module 1505 to be used in a non-sterile condition. Wired communication with electrodes in the catheter (not shown) is provided through lead 1520. In some embodiments, module 1505 may be designed to be sterilizable and reusable after each procedure and thus, not require a sterile bag 110. Module 1505 may be integrated into the catheter handle. Module 1505 may include a rechargeable battery. Module 1505 may include a non-rechargeable battery. Module 1505 may also be integrated into the catheter handle along with a battery, and the entire apparatus may be disposed of after a procedure.

Other embodiments of wireless module 1505 may be linked with medical devices other than catheters. For example, a blood pressure monitor, an oxygen saturation monitor, other types of catheters, etc. may use module 1505 to communicate wirelessly with data processing systems, reducing the amount of wired connections in the cath lab.

A catheter or other medical device coupled to a wireless transmitter and in wireless communication with a data processing system may form a bidirectional control loop. For example, catheter electrodes may wirelessly provide a data processing system with several catheter ECG waveforms. The data processing system may perform analysis, such determining an average correlation coefficient and comparing the coefficient to a threshold as illustrated in FIG. 11. The data processing system may then transmit a command back to the catheter module based on the analysis. For example, the data processing system may wirelessly command the catheter handle to illuminate a green light if the average correlation coefficient exceeds the threshold.

Figure 16:
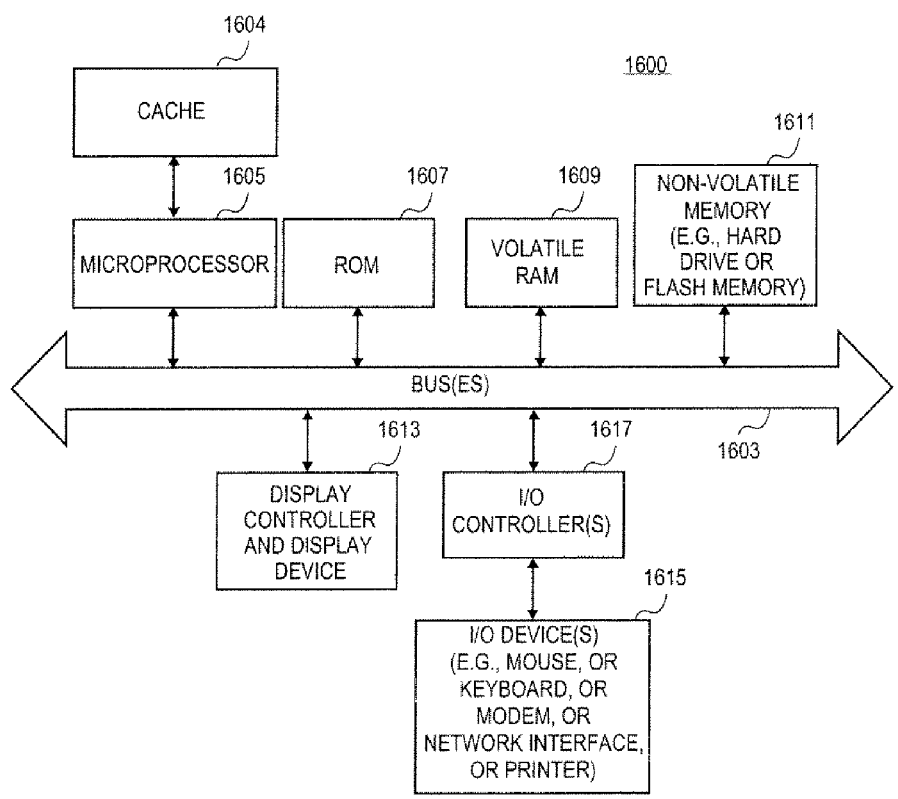
FIG. 16 is a diagram illustrating a data processing system that may be used by an embodiment of the invention.

FIG. 16 shows one example of a data processing system which may be used with one embodiment the present invention. For example, computer 115 in FIG. 1 may be implemented with a data processing system like the one illustrated in FIG. 16. Also, the wireless module 1505 in FIG. 15 may be implemented with a data processing system like the one illustrated in FIG. 16. Note that while FIG. 16 illustrates various components of a computer system, it is not intended to represent any particular architecture or manner of interconnecting the components as such details are not germane to the present invention. It will also be appreciated that network computers and other data processing systems which have fewer components or perhaps more components may also be used with the present invention.

As shown in FIG. 16, the computer system 1600, which is a form of a data processing system, includes a bus 1603 which is coupled to a microprocessor(s) 1605 and a ROM (Read Only Memory) 1607 and volatile RAM 1609 and a nonvolatile memory 1611. The microprocessor 1605 is coupled to cache 1604. The microprocessor 1605 may retrieve the instructions from the memories 1607, 1609, 1611 and execute the instructions to perform operations described above. The bus 1603 interconnects these various components together and also interconnects these components 1605, 1607, 1609, and 1611 to a display controller and display device 1613 and to peripheral devices such as input/output (I/O) devices which may be mice, keyboards, modems, network interfaces, printers and other devices which are well known in the art. Typically, the input/output devices 1615 are coupled to the system through input/output controllers 1617. The volatile RAM (Random Access Memory) 1609 is typically implemented as dynamic RAM (DRAM) which requires power continually in order to refresh or maintain the data in the memory.

The mass storage 1611 is typically a magnetic hard drive or a magnetic optical drive or an optical drive or a DVD RAM or a flash memory or other types of memory systems which maintain data (e.g., large amounts of data) even after power is removed from the system. Typically, the mass storage 1611 will also be a random access memory although this is not required. While FIG. 16 shows that the mass storage 1611 is a local device coupled directly to the rest of the components in the data processing system, it will be appreciated that the present invention may utilize a non-volatile memory which is remote from the system, such as a network storage device which is coupled to the data processing system through a network interface such as a modem, an Ethernet interface or a wireless network. The bus 1603 may include one or more buses connected to each other through various bridges, controllers and/or adapters as is well known in the art.

The present invention can relate to an apparatus for performing one or more of the operations described herein. This apparatus may be specially constructed for the required purposes, or it may comprise a general purpose computer selectively activated or reconfigured by a computer program stored in the computer. Such a computer program may be stored in a machine (e.g., computer) readable storage medium, such as, but is not limited to, any type of disk including floppy disks, optical disks, CD-ROMs, and magnetic-optical disks, read-only memories (ROMs), random access memories (RAMs), erasable programmable ROMs (EPROMs), electrically erasable programmable ROMs (EEPROMs), magnetic or optical cards, or any type of media suitable for storing electronic instructions, and each coupled to a bus.

A machine-readable storage medium includes any mechanism for storing information in a form readable by a machine (e.g., a computer). For example, a machine-readable storage medium includes read only memory ("ROM"); random access memory ("RAM"); magnetic disk storage media; optical storage media; flash memory devices; etc.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method of determining stability of a distal portion of a catheter, the method comprising:
monitoring, using a surface electrode, a first ECG signal originating from a skin surface of a patient;
monitoring, using an electrode on a distal portion of a catheter, a second ECG signal originating from a cardiac tissue of the patient;
extracting, by a processor, a plurality of first components from a recurring interval of the second ECG signal, wherein the first ECG signal defines a start time and a duration of the recurring interval;
comparing, by the processor, the plurality of first components to determine a first similarity value of the plurality of first components over time;
comparing, by the processor, the first similarity value to a predetermined threshold value to determine whether the distal portion of the catheter is stable.

2. The method of claim 1, further comprising:
performing an operational step;
extracting a plurality of second components from the recurring interval of the second ECG signal;
comparing the plurality of second components to determine a second similarity value of the plurality of second components over time;
comparing the second similarity value to the first similarity value to determine a change in stability of the distal portion of the catheter corresponding to performing the operational step;
providing a first indication if the change in stability indicates the operational step is successful;
providing a second indication if the change in stability indicates the operational step is unsuccessful.

3. The method of claim 1, further comprising:
providing a first indication if the first similarity value is greater than or equal to the predetermined threshold value;
providing a second indication if the first similarity value is less than the predetermined threshold value.

4. The method of claim 3, wherein the first indication comprises activating a first illumination on the catheter and wherein the second indication comprises activating a second illumination on the catheter.

5. The method of claim 1, wherein determining the first similarity value comprises determining a correlation coefficient of the plurality of first components over time.

6. The method of claim 1 wherein the first ECG signal is provided by a plurality of surface electrodes coupled to the skin surface of the patient and wherein the second ECG signal is provided by a plurality of electrodes coupled to the distal portion of the catheter.

7. The method of claim 2 wherein the operational step comprises extending a needle from a distal end of the catheter.

8. The method of claim 1, wherein monitoring the second ECG signal originating from the cardiac tissue of the patient comprises:
wirelessly transmitting data corresponding to the second ECG signal from a wireless transmitter coupled to the catheter to a data processing system.

9. The method of claim 3, wherein providing the first indication if the first similarity value is greater than or equal to the predetermined threshold value comprises:
wirelessly transmitting data representing a command to provide the first indication from a data processing system to a wireless receiver electrically coupled to the catheter.

10. A non-transitory machine-readable storage medium storing instructions which when executed by a data processing system cause the data processing system to perform a method of determining stability of a distal portion of a catheter, the method comprising:
monitoring, using a surface electrode, a first ECG signal originating from a skin surface of a patient;
monitoring, using an electrode on a distal portion of a catheter, a second ECG signal originating from a cardiac tissue of the patient;
extracting a plurality of first components from a recurring interval of the second ECG signal, wherein the first ECG signal defines a start time and a duration of the recurring interval;
comparing the plurality of first components to determine a first similarity value of the plurality of first components over time;
comparing the first similarity value to a predetermined threshold value to determine whether the distal portion of the catheter is stable.

11. The non-transitory machine-readable storage medium of claim 10, the method further comprising:
performing an operational step;
extracting a plurality of second components from the recurring interval of the second ECG signal;
comparing the plurality of second components to determine a second similarity value of the plurality of second components over time;
comparing the second similarity value to the first similarity value to determine a change in stability of the distal portion of the catheter corresponding to performing the operational step;
providing a first indication if the change in stability indicates an increase in stability;
providing a second indication if the change in stability indicates a decrease in stability.

12. The non-transitory machine-readable storage medium of claim 10, the method further comprising:
providing a first indication if the first similarity value is greater than or equal to the predetermined threshold value;
providing a second indication if the first similarity value is less than the predetermined threshold value.

13. The non-transitory machine-readable storage medium of claim 12, wherein the first indication comprises activating a first illumination on the catheter and wherein the second indication comprises activating a second illumination on the catheter.

14. The non-transitory machine-readable storage medium of claim 10, wherein determining the first similarity value comprises determining a correlation coefficient of the plurality of first components over time.

15. The non-transitory machine-readable storage medium of claim 10 wherein the first ECG signal is provided by a plurality of surface electrodes coupled to the skin surface of the patient and wherein the second ECG signal is provided by a plurality of electrodes coupled to the distal portion of the catheter.

16. The non-transitory machine-readable storage medium of claim 11 wherein the operational step comprises extending a needle from a distal end of the catheter.

17. The non-transitory machine-readable storage medium of claim 10, wherein monitoring the second ECG signal originating from the cardiac tissue of the patient comprises:
wirelessly transmitting data corresponding the second ECG signal from a wireless transmitter coupled to the catheter to a data processing system.

18. The non-transitory machine-readable storage medium of claim 12, wherein providing a first indication if the first similarity value is greater than or equal to the predetermined threshold value comprises:
wirelessly transmitting data representing a command to provide the first indication from a data processing system to a wireless receiver electrically coupled to the catheter.

19. An apparatus for use in a medical procedure to determine stability of a distal portion of a catheter, the apparatus comprising:
a first input configured to receive a first ECG signal from a surface electrode disposed on a skin surface of a patient, the first ECG signal originating from a skin surface of the patient;
a second input configured to receive a second ECG signal from an electrode on a distal portion of a catheter within a heart chamber of the patient, the second ECG signal originating from a cardiac tissue of the patient;
a processing system coupled to the first input and to the second input, the processing system configured to:
monitor the first ECG signal and the second ECG signal;
extract a plurality of samples from the second ECG signal based on a start time and a duration of the first ECG signal;
compare the plurality of samples to determine whether the distal portion of the catheter is stable relative to the cardiac tissue.

20. The apparatus of claim 19, wherein the processing system is further configured to:
extract the samples from a recurring interval of the second ECG signal, the recurring interval defined by the start time and the duration; and
determine a first similarity value based on comparing the plurality of samples.

* * * * *